US006709391B2

(12) United States Patent
Mesaros et al.

(10) Patent No.: US 6,709,391 B2
(45) Date of Patent: Mar. 23, 2004

(54) DIAGNOSTIC ULTRASOUND SYSTEM CART WITH LATERALLY ARTICULATING CONTROL PANEL

(75) Inventors: Robert Mesaros, Bothell, WA (US); Yas Matsui, Redmond, WA (US); Jay Wilkins, Belgrade, MT (US); William Hollman, Lake Forest Park, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 37 days.

(21) Appl. No.: 10/155,459

(22) Filed: May 23, 2002

(65) Prior Publication Data

US 2003/0220565 A1 Nov. 27, 2003

(51) Int. Cl.⁷ .................................................. A61B 8/14
(52) U.S. Cl. ....................................................... 600/437
(58) Field of Search ................................. 600/437–472

(56) References Cited

U.S. PATENT DOCUMENTS

| 4,870,954 | A | | 10/1989 | Satoh | |
|---|---|---|---|---|---|
| 5,129,397 | A | * | 7/1992 | Jingu et al. | 600/437 |
| D360,690 | S | * | 7/1995 | Murakami | 600/437 |
| D368,521 | S | * | 4/1996 | Asai et al. | 600/437 |
| 5,924,988 | A | * | 7/1999 | Burris et al. | 600/437 |
| 6,312,381 | B1 | | 11/2001 | Knell et al. | |

FOREIGN PATENT DOCUMENTS

EP  0 415 323 A2  8/1990

* cited by examiner

*Primary Examiner*—Marvin M. Lateef
*Assistant Examiner*—William C Jung
(74) *Attorney, Agent, or Firm*—W. Brinton Yorks, Jr.

(57) ABSTRACT

The control panel of an ultrasound system can be moved laterally from one side of the ultrasound system to the other, enabling an operator to more comfortably operate the ultrasound system while scanning a patient located to the side of the ultrasound system. The control panel locks in its central home position and can be moved linearly to either side of the home position. Detents serve to retain the control panel at different lateral locations. Preferably the control panel can swivel independently of its lateral articulation.

15 Claims, 16 Drawing Sheets

DIAGNOSTIC ULTRASOUND SYSTEM CART WITH LATERALLY ARTICULATING CONTROL PANEL

This invention relates to ultrasonic diagnostic imaging systems and, in particular, to ultrasound systems with control panels that articulate laterally.

Cart-borne ultrasound systems are convenient to use in a hospital, as they can be used in a dedicated imaging lab where they are essentially stationary, or can be rolled to a patient's bedside when a medical condition or other expedient dictates. When the ultrasound exam is being conducted at bedside, the clinician is applying the ultrasound probe to the patient in the bed while manipulating the controls of the ultrasound system located next to the bed. Often it is not possible to position the ultrasound system close enough to the patient bed so that scanning can be conducted comfortably. The bedframe or restraining bar can prevent the ultrasound system from being moved in close proximity to the patient. As a result, the clinician must extend to reach the ultrasound system controls while trying to hold the ultrasound probe in contact with the patient's body. The required contortions can be exhausting and potentially debilitating. It would be desirable to be able to locate the control panel in close proximity to the patient even when the ultrasound system is relatively removed from the patient, and to do so adjustably for a particular exam setting.

In accordance with the principles of the present invention a control panel for a cart-borne ultrasound system is provided which can be articulated laterally. Preferably the control panel can be moved laterally in both directions relative to a nominal center position to accommodate an exam being conducted on either side of the ultrasound system. In a given embodiment the control panel may slide smoothly from side to side, or may move through a plurality of lateral detent positions. It is preferred that the control panel have a center lock position in either case. Preferably the control panel also swivels, so that it can be moved laterally to the side of the ultrasound system cart, then swiveled to oppose the operator in a comfortable position.

Figure 1:
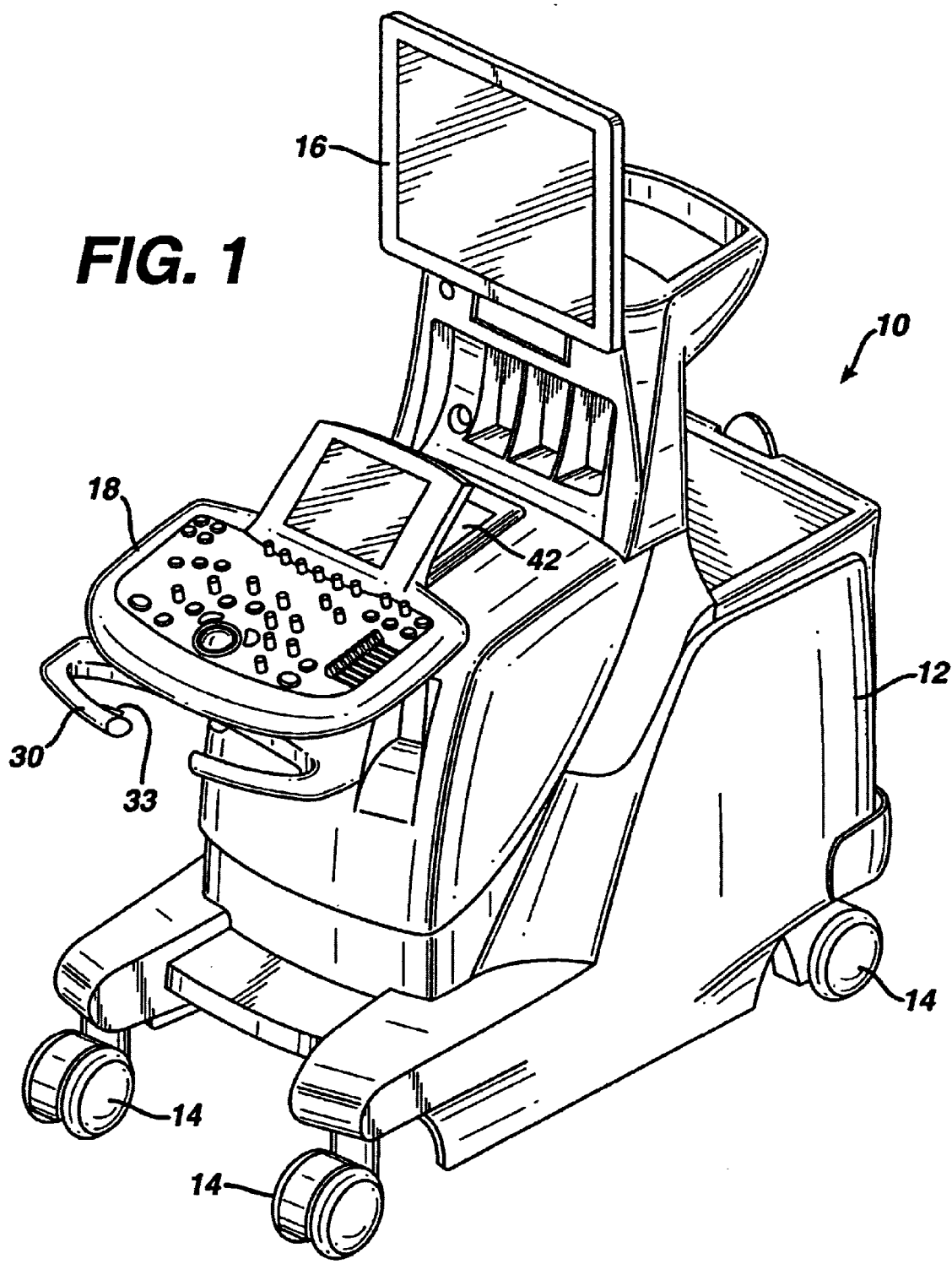
FIG. 1 illustrates a cart-borne ultrasound system in perspective.

Referring first to FIG. 1, a cart-borne ultrasound system 10 is shown in perspective. The cart includes an electronics bay 12 inside of which are located printed circuit boards for electronically processing received ultrasound signals. The ultrasound signals are processed to produce an image which is displayed on a display 16, the plane of which is aligned with an approximate laterally extending center line of the cart. The cart is mounted on wheels or casters 14 so that it can be rolled to a lab or a patient's bedside. In the front of the cart is a control panel 18 which contains a number of knobs, buttons, slide switches, and a trackball by which a user operates the ultrasound system. The control panel is mounted above a handle 30 which extends from the front of the ultrasound system. The handle 30 can be used to pull the cart to move it from one location to another. On the inside of the handle 30 is a handle lock release 33 which will be discussed below.

Figure 2:
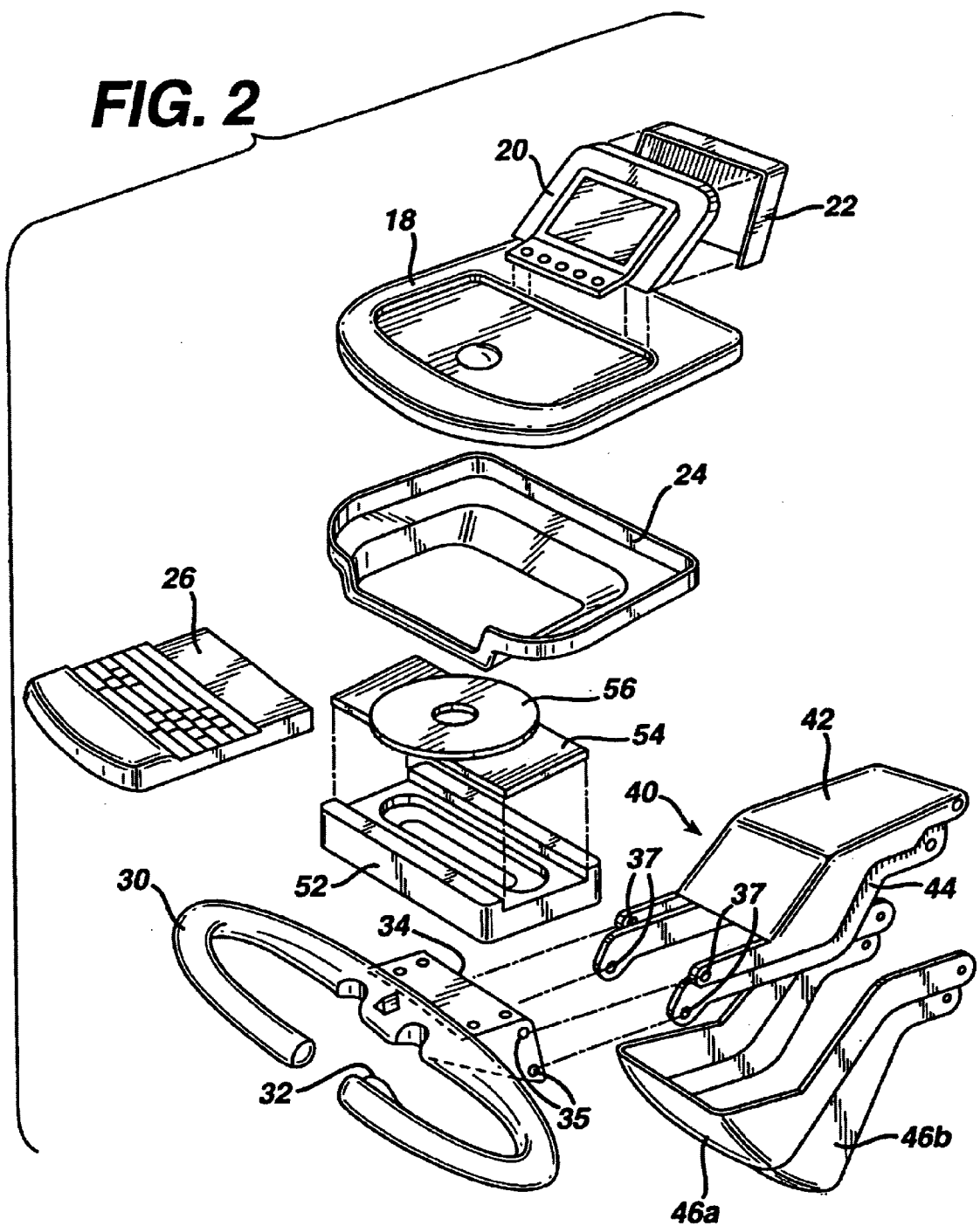
FIG. 2 is an exploded view of a control panel articulation assembly in accordance with a first embodiment of the present invention.

FIG. 2 is an exploded view of a control panel articulation assembly in accordance with a first embodiment of the present invention. The control panel 18 is mounted on a lift mechanism 40 which serves to elevate and lower the control panel to a height which is comfortable for the user. The lift mechanism 40 is more fully described in concurrently filed U.S. patent application Ser. No. 10/15.4,733, filed May 23, 2002. As described therein, the lift mechanism 40 includes a pivotally mounted lift top 42 and lift bottom 44 which are mounted to the ultrasound system cart at the rear of the mechanism. The lift mechanism 40 also includes lift assembly beard covers 46a and 46b, which prevent the appearance of pinch points beneath the lift top and bottom when the control panel is in an elevated position. When the user depresses a lift release 32 in the handle, the lift mechanism moves freely to raise and lower the control panel. When the lift release 32 is released, the lift mechanism locks in its current position.

The control panel includes a touchscreen 20 and touchscreen rear cover 22 which are mounted on the control panel 18. Below the control panel is a control panel bottom 24. A keyboard 26 can slide into and out of the compartment in the control panel bottom. The control panel bottom is mounted on a swivel plate 56 which rotates about a central pivot point. The swivel plate 56 is mounted on a lateral carriage 54. The lateral carriage can be moved laterally in the mating opening of a lateral track 52. The lateral track 52 is mounted on the top of a connection block 34, to which the handle 30 is also connected. The connection block 34 is movably mounted to the lift mechanism 40 through holes 35 and 37.

Figure 3:
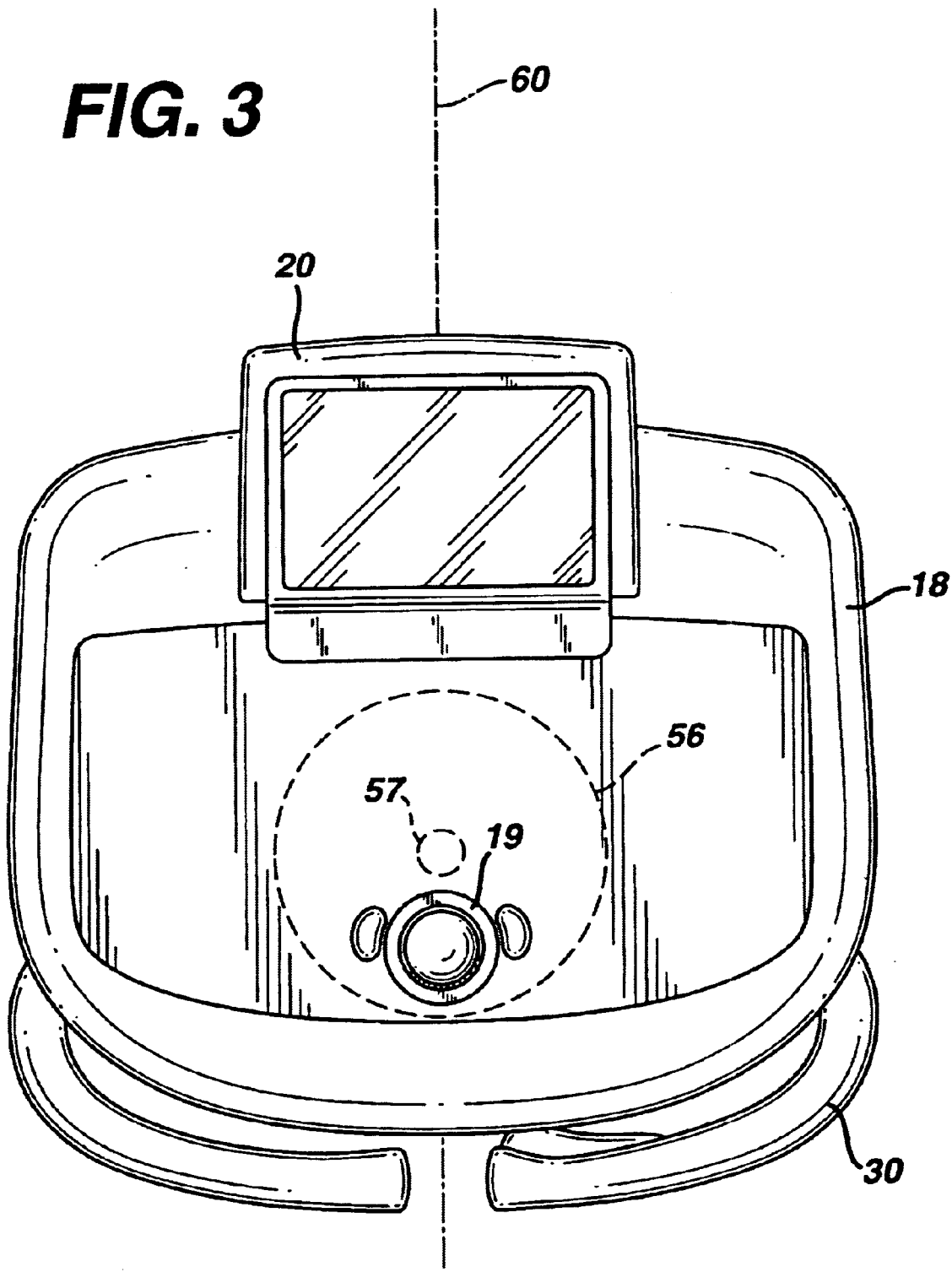
FIGS. 3–8 illustrate the range of control panel articulation provided by the first embodiment.

FIGS. 3–8 illustrate the range of control panel motion provided by the swivel plate 56, the lateral carriage 54, and the lateral track 52 of FIG. 2. In FIG. 3 the control panel 18 is shown in its nominal center (home) position as it appears in FIG. 1. The control panel can be locked firmly in this position. In this position the control panel is centered on a center axis 60, which will generally be aligned with the center of the ultrasound system cart as shown in FIG. 1. The swivel plate 56 and its central pivot point 57 are shown in phantom on the control panel 18, just behind the location of the trackball 19.

Figure 4:
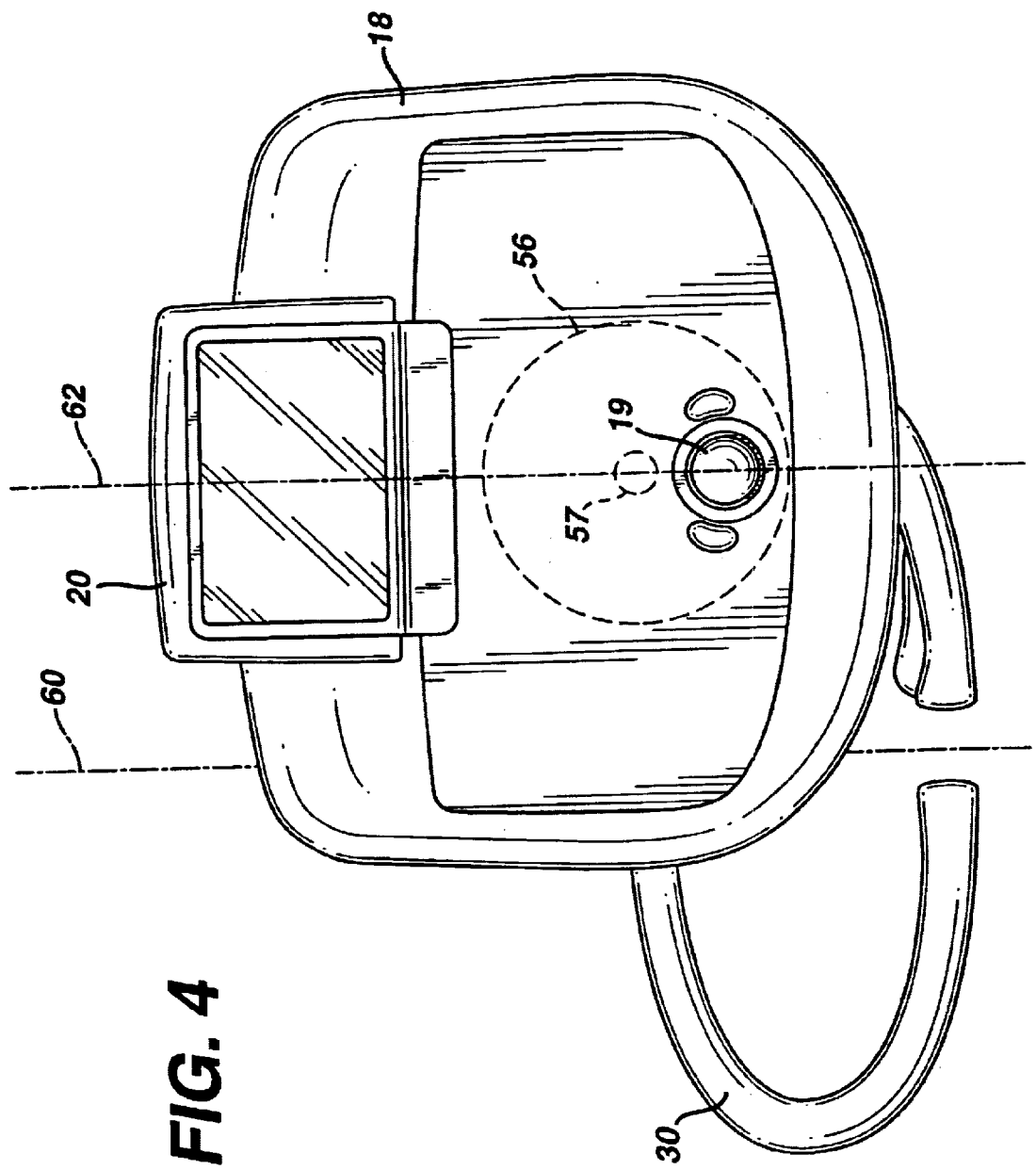

In FIG. 4 the control panel has been moved laterally to the right by moving the lateral carriage 54 in the lateral track 52. The carriage may move smoothly in a frictional engagement with the track, or preferably it may move through a series of detent positions provided by detent recesses and a ball plunger or hinge plate or other detent mechanism. Since the lateral track is linear in this embodiment the control panel will move laterally in a straight line until it reaches the terminus of its range of lateral motion. In a constructed embodiment the control panel was allowed to move laterally ±5 inches from its home position in alignment with center line, 60. In its rightmost location shown in FIG. 4 the control panel is centered on a laterally displaced center line 62.

Figure 5:
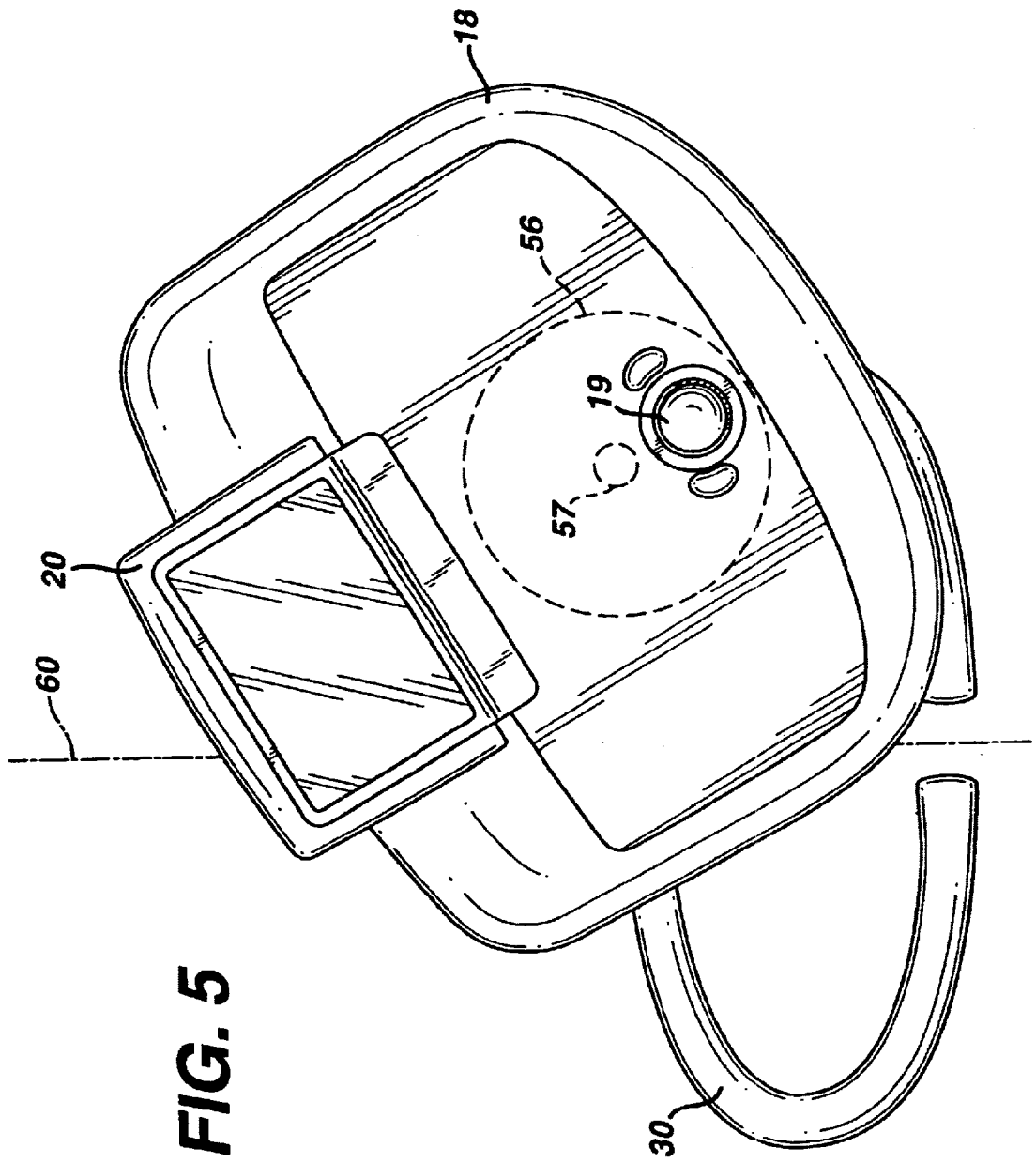

In FIG. 5 the control panel 18 has been moved laterally by operation of the carriage 54 in track 52, and has also been rotated by operation of the swivel plate 57 rotating about its center pivot point 57. This position of the control panel would serve an operator scanning a patient on the right side of the ultrasound system cart and who is also to the right of the cart. The operator does not have to reach or stretch to access the control panel, as the control panel has been moved laterally and swiveled to a comfortable position for the operator.

Figure 6:
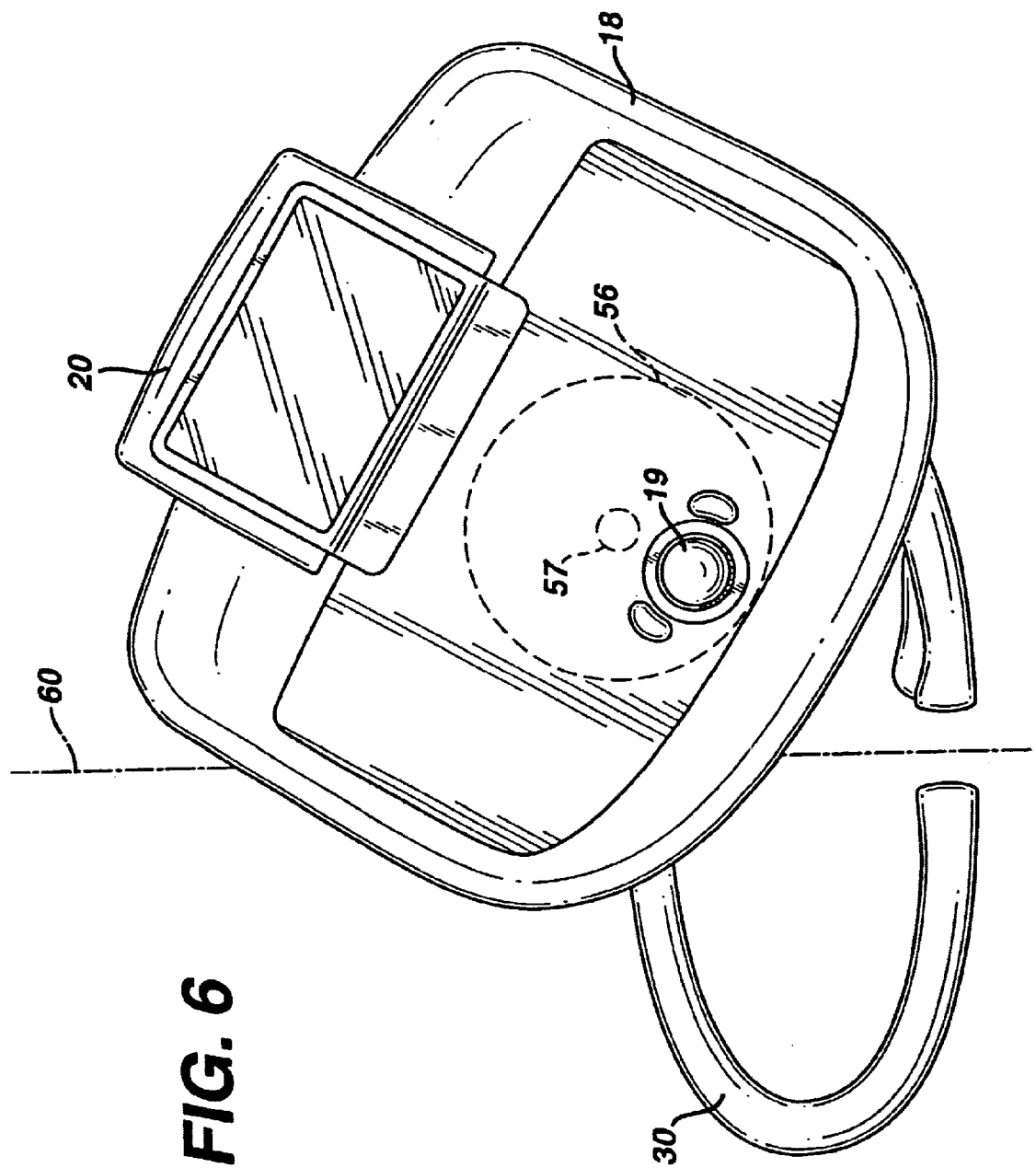

In FIG. 6 the operator has moved the control panel laterally to the right and has swiveled the control panel clockwise about 30°. The combination of the lateral movement and swiveling gives the operator the sense that the control panel has rotated about his operating position or location in the center of the cart. In accordance with one aspect of the present invention, this sense of rotation about the operator position is enhanced by locating the axis of the pivot point 57 of the swivel plate in the front half of the control panel 18. In prior art ultrasound systems the pivot point for the control panel has been located at the back of the control panel or, at best, in the center of the control panel. When the control panel is swiveled about these pivot points, the operator has the impression that the control panel is swinging away from the operator location in front of the control panel, and in many cases this is in fact what is happening. By locating the pivot point for swiveling the control panel in front of the control panel center, the operator can adjust the control panel about his central operating position for the ultrasound system.

Figure 7:
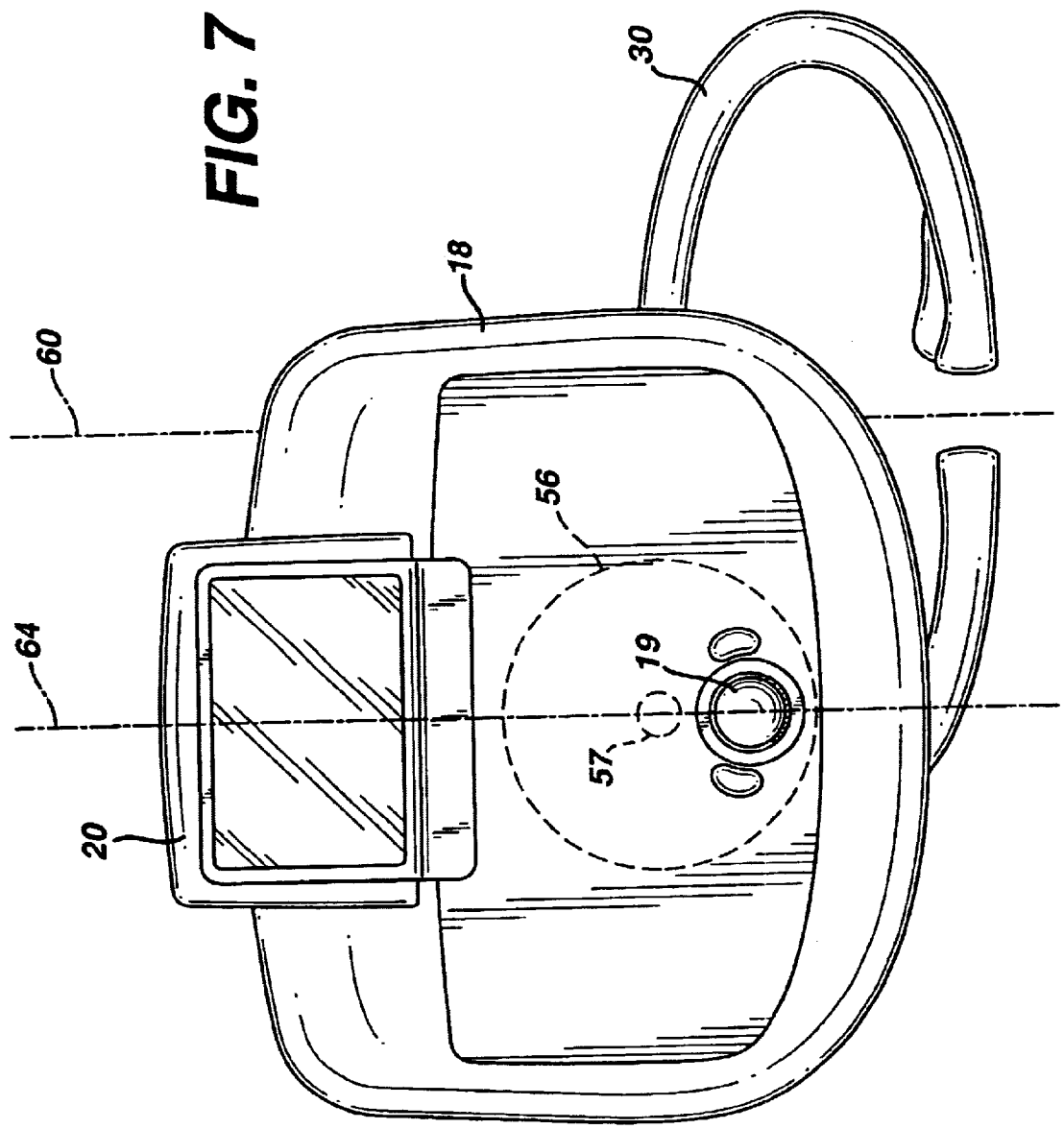
Figure 8:
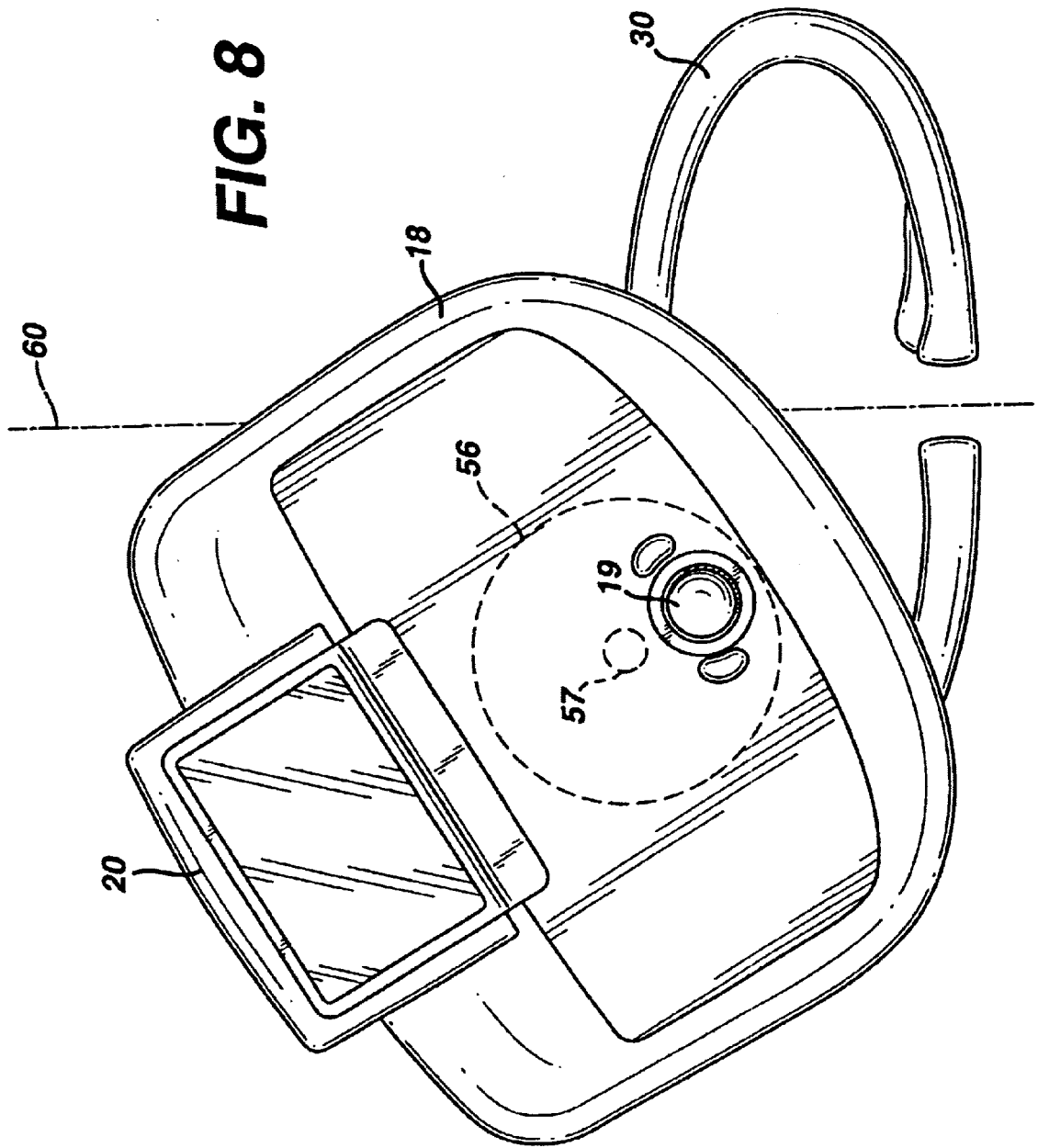

FIG. 7 illustrates the position of the control panel 18 when it has been laterally moved to the left of the center axis 60 and into central alignment with a new center line 64 which has been displaced to the left. As FIG. 8 shows, the control panel 18 can be swiveled about the pivot point 57 in a counter-clockwise direction to effectively rotate the control panel to the left.

Figure 9:
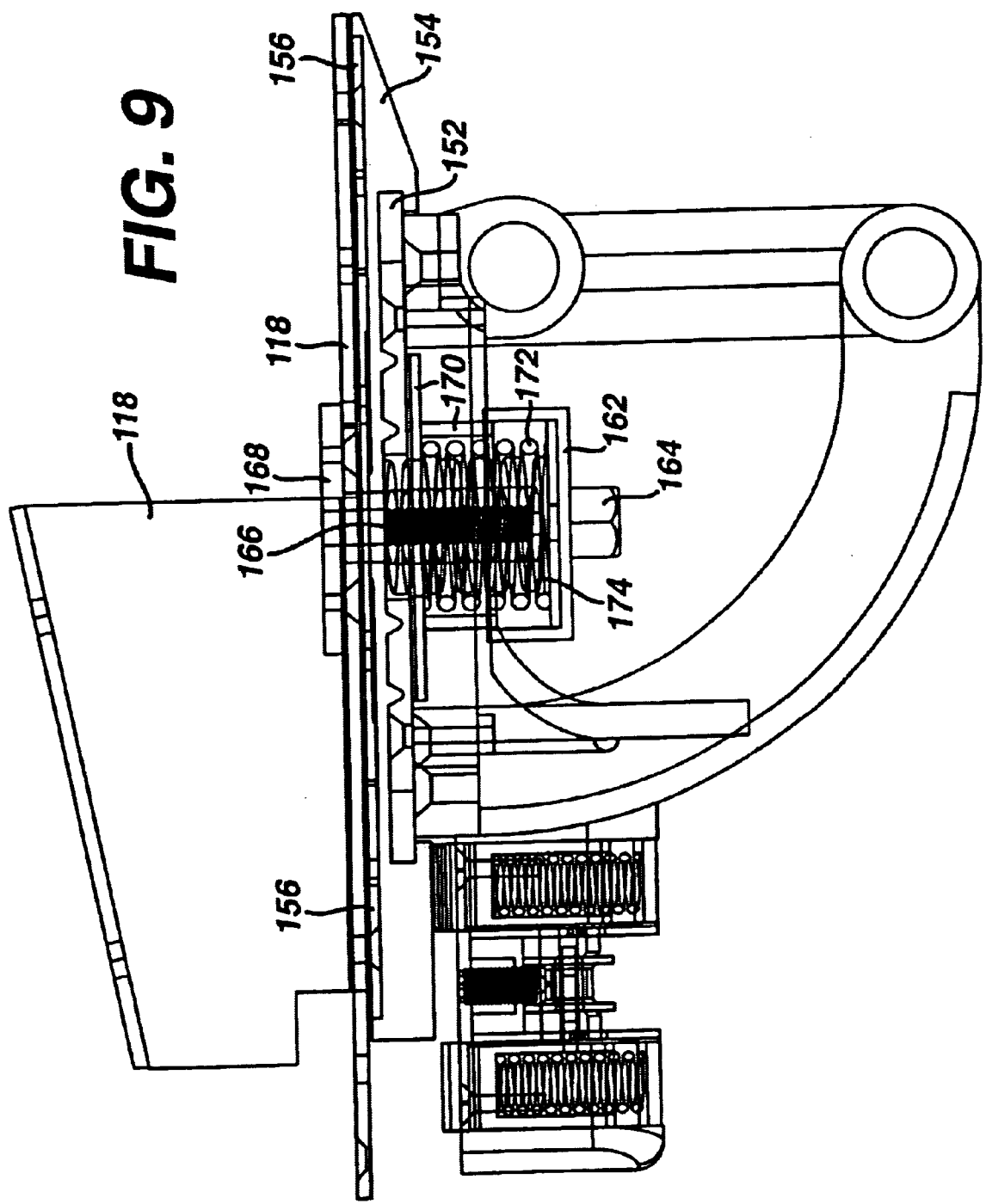
FIG. 9 illustrates a mechanism for adjusting the friction of a control panel articulation assembly.

The preferences of users for the ease with which the control panel can be articulated are widely variable. Some users may prefer that the control panel be easily articulated with the application of only light force, while others may prefer that the control panel articulate only in response to a firmer pressure. To accommodate these differing preferences FIG. 9 illustrates a mechanism for adjusting the rotational and translational friction of the control panel. This illustrated embodiment advantageously enables both frictional factors to be adjusted by a single control. FIG. 9 illustrates the frame 118 of a control panel which is attached to two semicircular swivel bearings 156. The swivel bearings travel in curved slots in a base 154 as the control panel swivels. The base is mounted on a translation bearing 152. The control panel assembly moves laterally against the translation bearing as the control panel is moved laterally. In a preferred embodiment the bearings are fabricated from low friction polyethylene.

The adjustment mechanism comprises an adjustment shaft 162 which has an adjustment nut 164 on the bottom. The adjustment shaft has a central screw 166 which threads into a threaded aperture in a control panel shaft 168. The control panel shaft is fastened to the control panel frame 118. Located around the adjustment shaft and journaled to fit inside of the adjustment shaft is a translation disk 170. The translation disk slides against the lower surface of the translation bearing when the control panel is moved laterally.

The adjustment shaft and translation disk enclose an outer translation spring 172 and an inner rotation spring 174. The lower ends of both springs bear against the inner surface of the adjustment shaft. The upper end of the translation spring 172 bears against the inner surface of the translation disk 170, and the upper end of the rotation spring 174 bears against the base 154. The translation spring 172 thus controls the translational friction by controlling the force with which the translation disk bears against the translation bearing 152. The rotational spring controls the rotational friction by controlling the force which sandwiches the swivel bearings 156 between the control panel frame 118 and the base 154. The spring sizes and constants are chosen in conjunction with the range of travel of the screw 166 of the adjustment shaft to provide the desired range of frictional adjustment. As the adjustment nut 164 is turned to screw the screw 166 into the control panel shaft 168, the two springs are compressed, which increases both the rotational friction and the translational friction. Turning the adjustment nut 164 to withdraw the screw 166 from the control panel shaft reduces both frictional factors. In a constructed embodiment the rotational spring constant was chosen to provide a range of 40–56 in.-lbs. of torsional force, and the translational spring constant was chosen to provide a range of 5–8 lbs. of translational breaking force.

Figure 10:
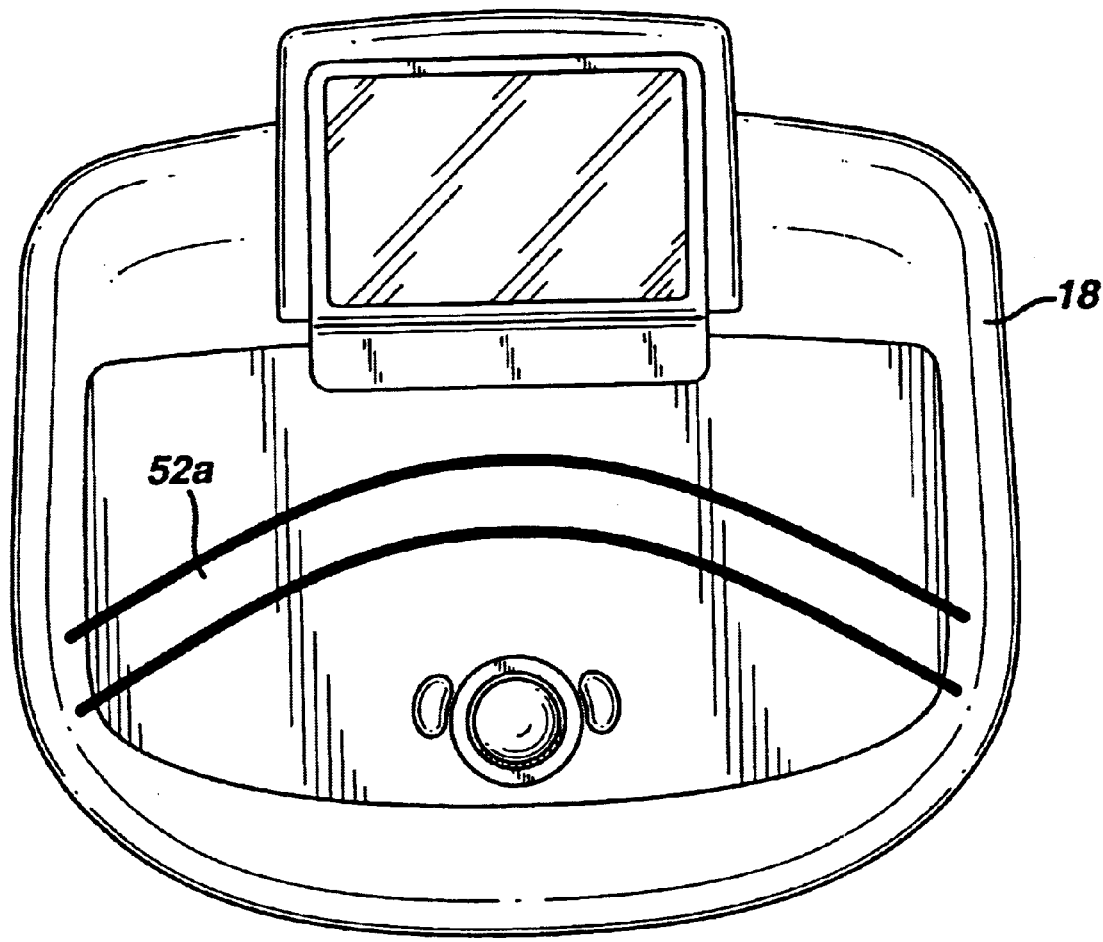
FIGS. 10–12 illustrate the control panel articulation provided by a curved path along which the control panel may move in accordance with a second embodiment of the present invention.
Figure 11:
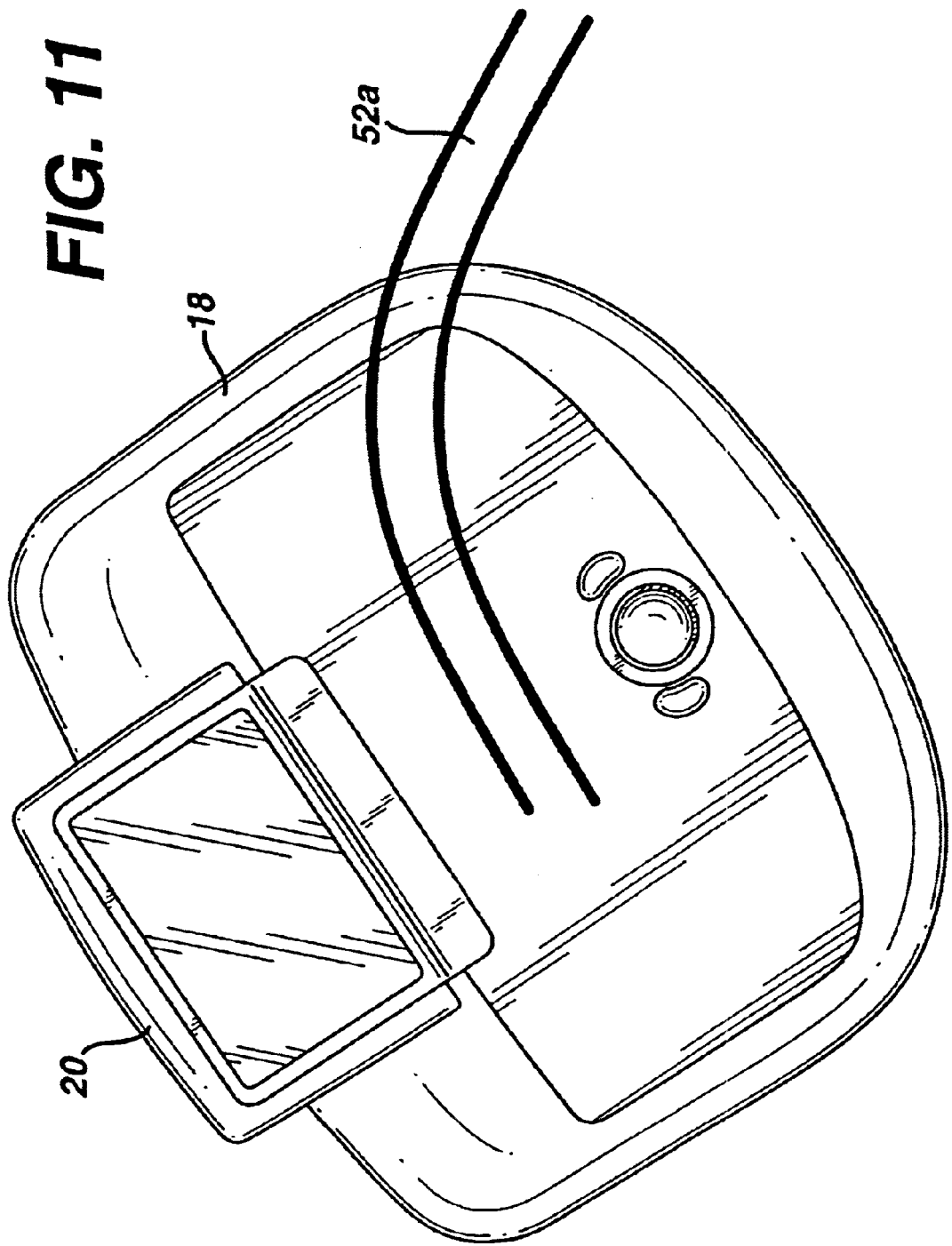
Figure 12:
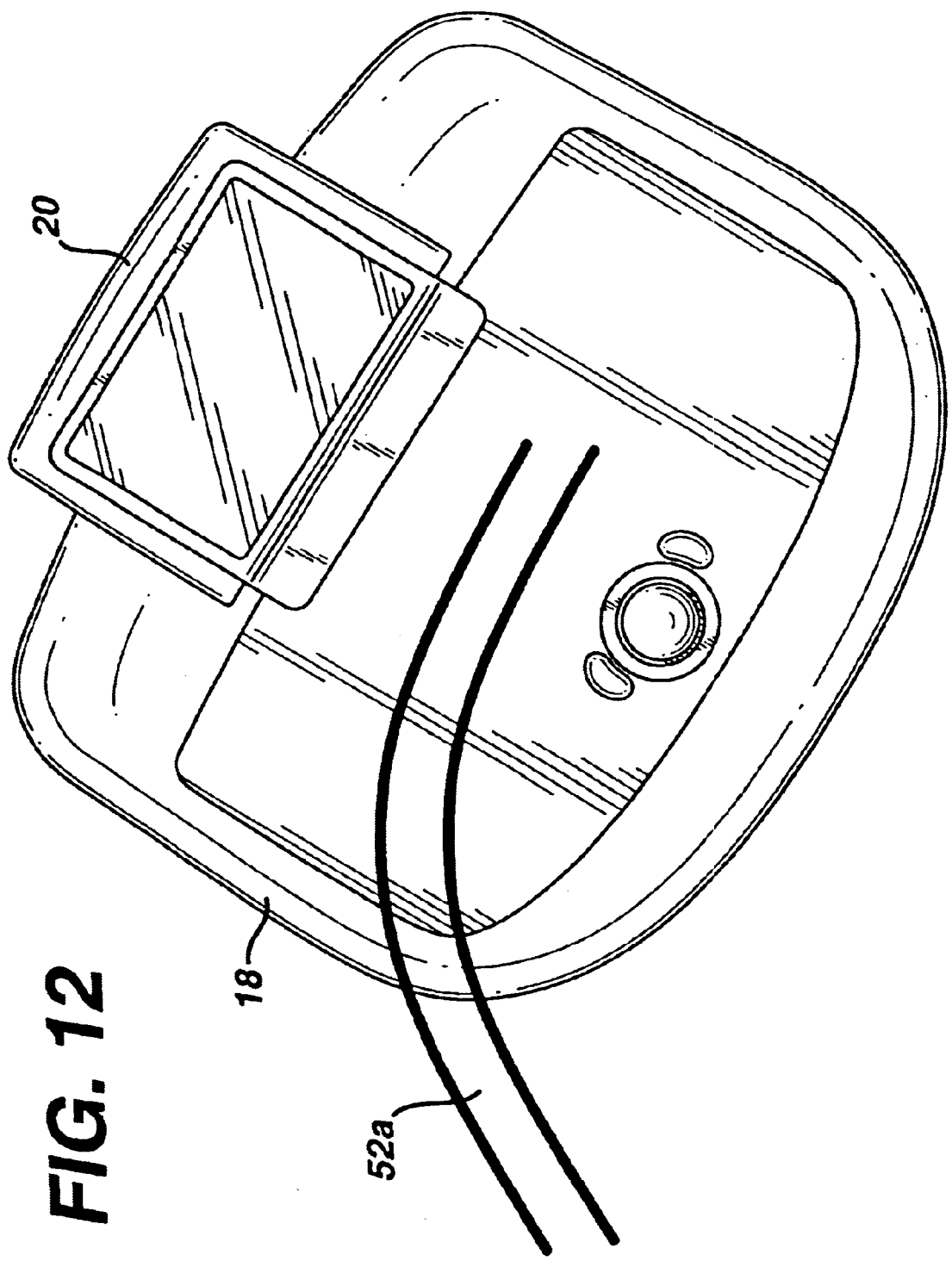

FIG. 10 illustrates a second embodiment of the present invention in which the path of travel of the lateral track 52 is curved about the operator location in front of the control panel 18. The curved track 52a is drawn on top of the control panel for clarity of illustration. The lateral carriage 54 may be matchingly curved to ride in the arcuate track. Alternatively the lateral carriage may comprise track guides or pins which will slide along two arcuate grooves either smoothly or through a series of detent positions. The curved path may also comprise one or more curved rods or bars to which the control panel is movably attached. As FIG. 11 shows, as the control panel moves around the curved path it moves in an arc around the operator location in front of the ultrasound system. FIG. 12 shows the control panel when it is moved to the right along the curved path. When positioned in a desired location along the curved path, the control panel may be swiveled on the swivel plate 56, when used, so as to present a comfortable orientation in which the operator can control the ultrasound system while scanning the patient.

Figure 13:
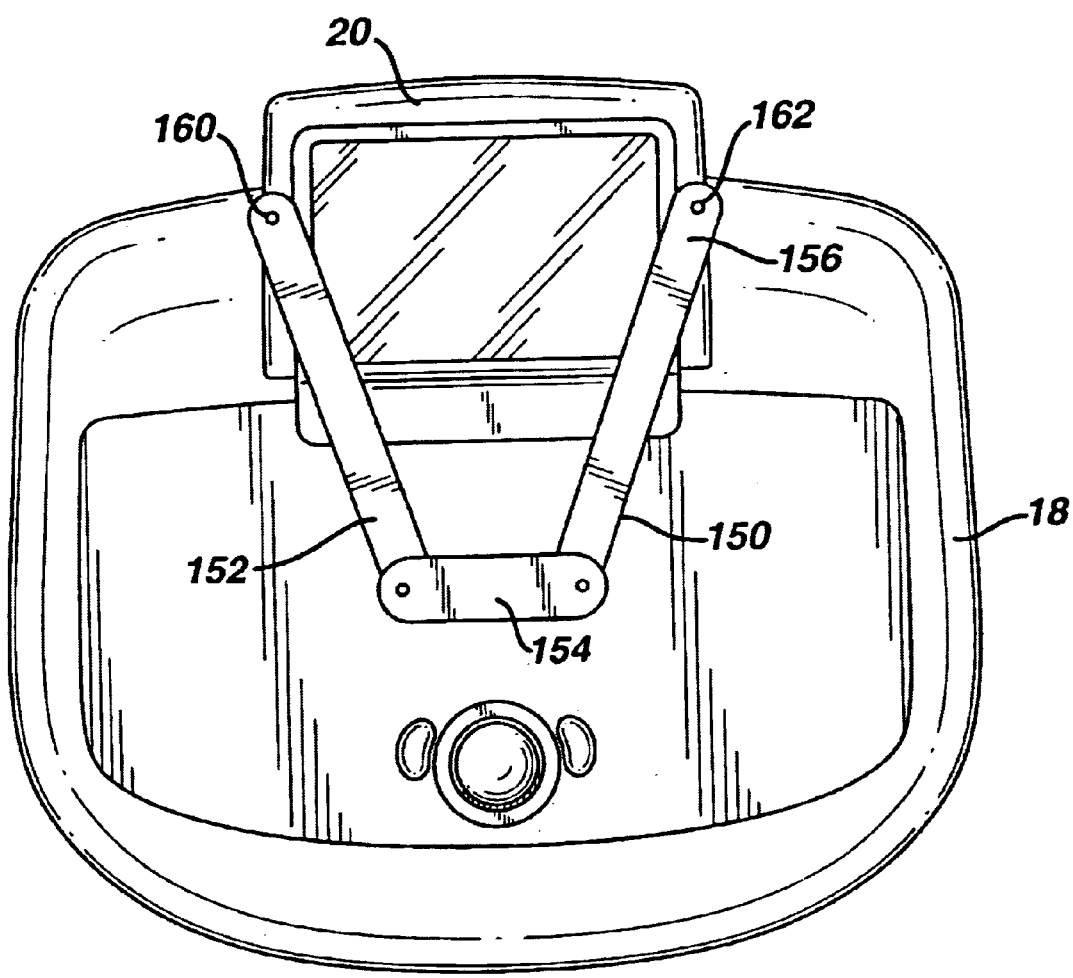
FIGS. 13–15 illustrate the control panel articulation provided by a pivoting articulation assembly of a third embodiment of the present invention.
Figure 14:
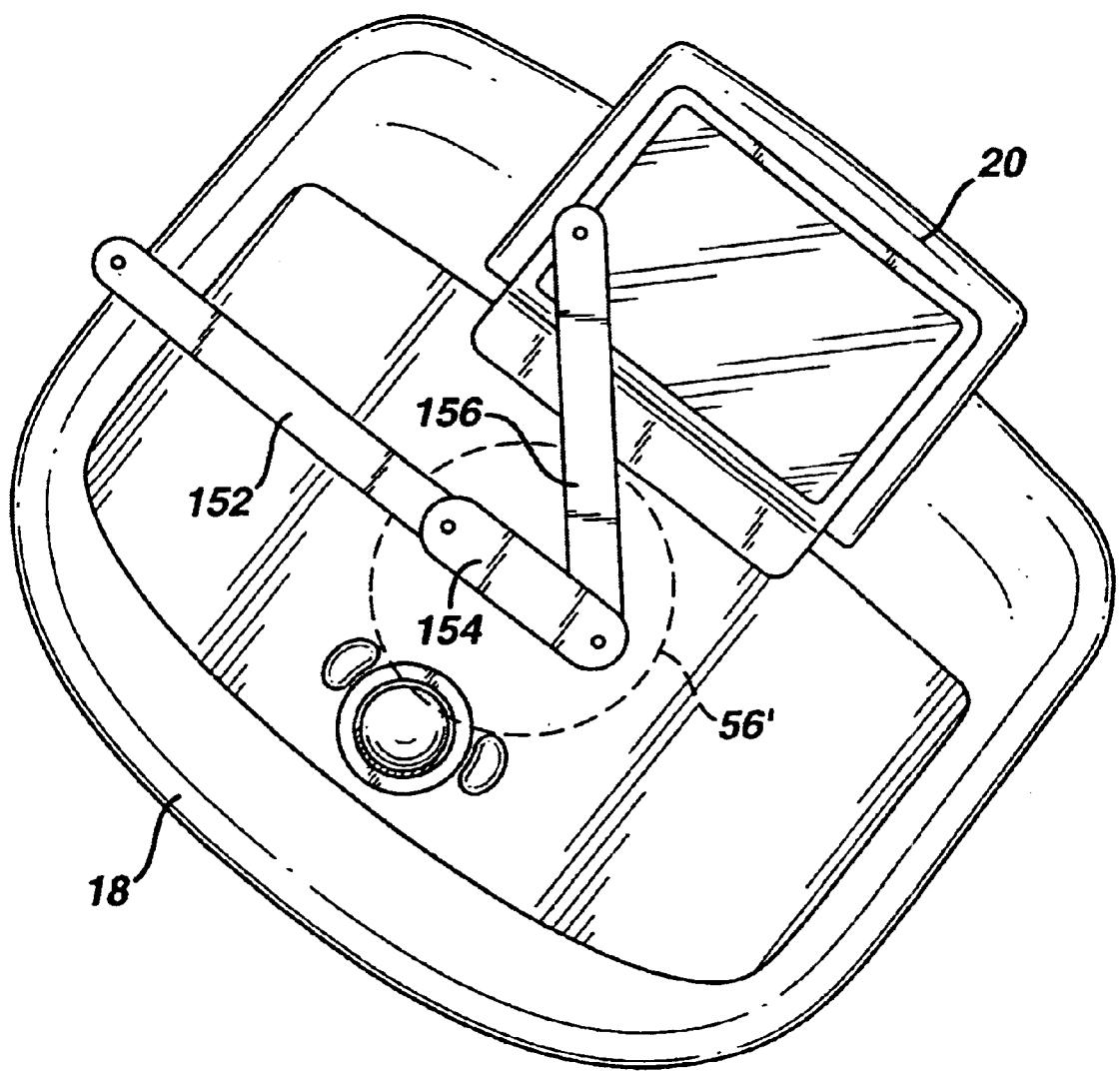
Figure 15:
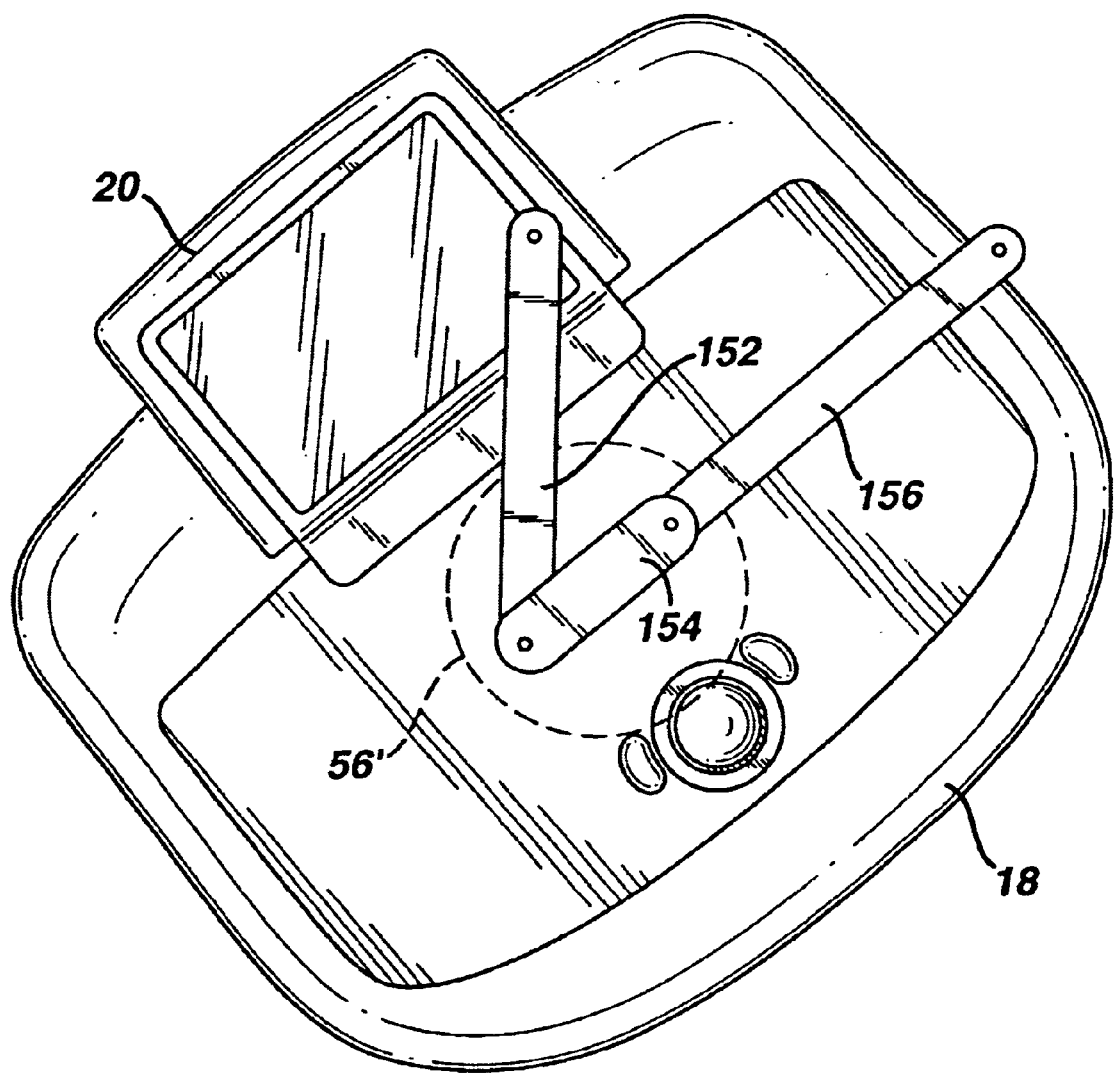

FIG. 13 illustrates a third embodiment of the present invention in which the position of the control panel is adjusted by articulation of a pivoting assembly 150 in place of the carriage and track of the previous embodiments. Again, the assembly 150 is drawn on top of the control panel for clarity of illustration. The illustrated assembly comprises three links which are pivotally connected to each other. Links 152 and 156 are connected to the cart by pivot connections 160 and 162 to the connection block or other point on the cart. The swivel plate, if used, is connected to the central link 154. FIG. 13 illustrates the orientation of the links when the control panel is in its central home position. In FIG. 14 the control panel has been moved to the right. As it moves the links pivot around their four pivot points to assume the position shown in FIG. 14. The motion of the control panel is arcuate, similar to the control panel motion in the second embodiment, and as it moves laterally it also moves forward. FIG. 15 illustrates the position of the control panel when swinging to the left on the pivoting assembly 150. As the phantom outline 56' of the swivel plate shows, the control panel may be swiveled at any location in its arcuate path of travel. As in the previous embodiments, the operator is able to swing the control panel about his central operating position, then swivel the control panel to the most comfortable system operating position.

Figure 16:
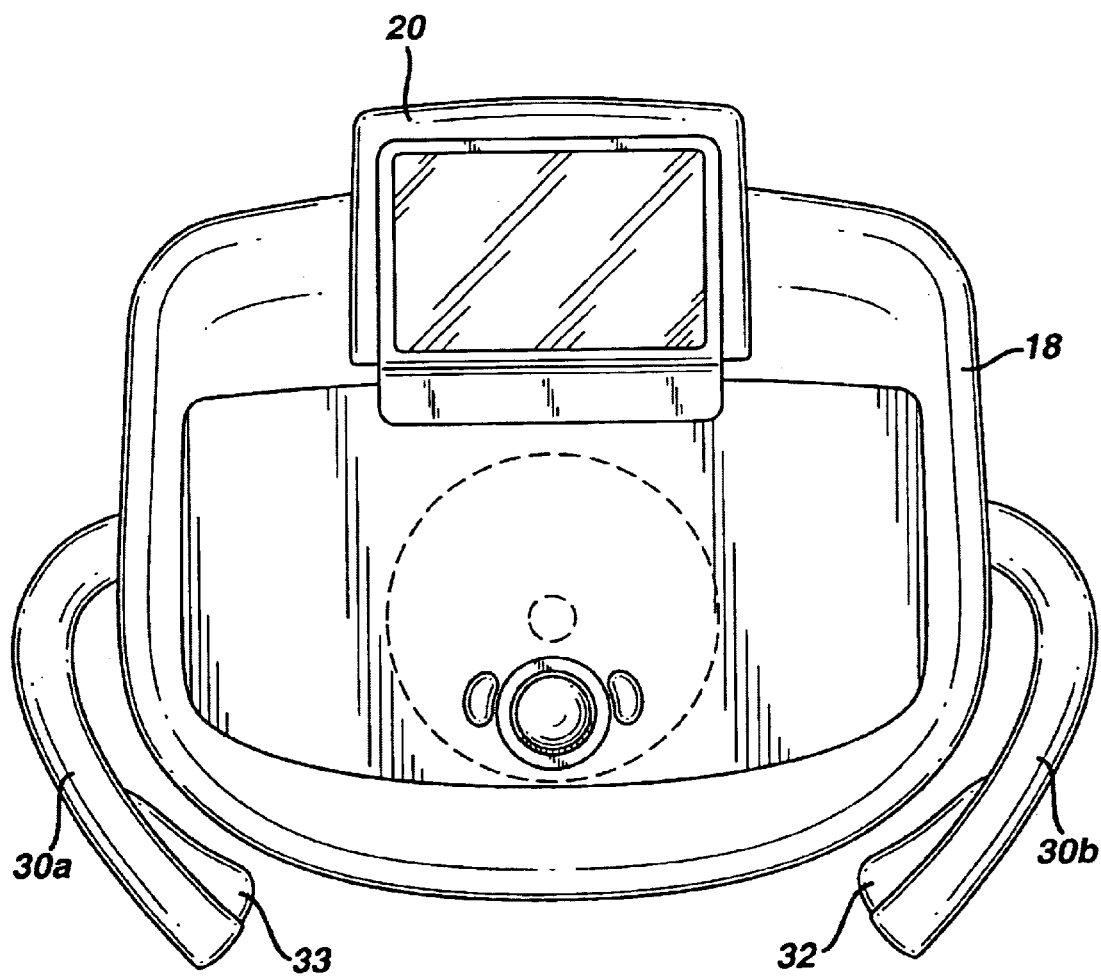
FIG. 16 illustrates an articulating cart handle in accordance with the principles of the present invention.

In the embodiment shown in FIGS. 1 and 2 the handle 30 is seen to be located below the control panel and extends forward from the location of the control panel. The handle 30 has several uses. It may be used to push or pull the mobile ultrasound cart. The handle can also be used to raise or lower the control panel elevation when the lift release button 32 in the handle is depressed. The handle may also be used to swivel the control panel or to move it laterally, although this may also be done by grasping the sides of the control panel to move it. In some operating situations, however, it may be that the handle is inconveniently located for comfortable scanning and system operation. For instance, when the control panel is lowered over the lap of an operator who is sitting, the handle may interfere with the legs of the operator or may prevent the operator from being as close to the front of the control panel as desired. In accordance with another aspect of the present invention, the handle may be moved out of the way as shown in FIG. 16. The handle lock release 33 is depressed to allow the handle 30 to split into two halves 30a and 30b, which can then be pivoted to the sides of the control panel as shown in the drawing. In this position the handle does not impede the operator during scanning. When scanning is completed and the handle is to be used to pull the cart-borne ultrasound system to a new location, the handle halves are swung back to their original center positions where they lock into place. The handle 30 is then rigidly positioned for pulling the cart or raising or lowering the control panel. In other embodiments unlocking the handle can permit the entire handle to swing or slide to one side of the control panel, in which case the handle can be fabricated as a single unit rather than separate halves.

Modifications to the foregoing embodiments will readily occur to those skilled in the art. The second and third embodiments may be used with or without the swivel capability, for instance. Mechanisms different from those shown above may be employed to give the control panel the described adjustment characteristics.

What is claimed is:

1. A cart-borne ultrasound system including a movable cart; electronic circuitry located on the cart which processes ultrasound signals for the formation of ultrasound images, and a display coupled to the circuitry for the display of ultrasound images, comprising:
    a control panel facing the front of the ultrasound system when located in a home position and coupled to the electronic circuitry for user control of the ultrasound system; and
    a laterally articulating connection coupled to the control panel which permits the control panel to be moved laterally to either side of the home position without moving toward the rear of the ultrasound system.

2. The cart-borne ultrasound system of claim 1, wherein the laterally articulating connection allows the control panel to be moved linearly through a series of positions including the home position.

3. The cart-borne ultrasound system of claim 2, wherein the series of positions are detented.

4. The cart-borne ultrasound system of claim 1, wherein the control panel can be locked in the home position.

5. The cart-borne ultrasound system of claim 1, further comprising a swivel connection coupled to the control panel which permits the control panel to be independently swiveled about a pivot point at a plurality of lateral locations.

6. The cart-borne ultrasound system of claim 5, wherein the laterally articulating connection permits the control panel to be linearly articulated between left and right terminus positions, and wherein the swivel connection permits the control panel to be swiveled through an angle of rotation of at least 30°.

7. The cart-borne ultrasound system of claim 1, wherein the laterally articulating connection is a non-pivoting mechanism.

8. The cart-borne ultrasound system of claim 7, wherein the laterally articulating connection comprises a track coupled to the cart and a carriage coupled to the control panel which engages the track.

9. The cart-borne ultrasound system of claim 8, wherein the track comprises an opening, a rod, a bar, or a groove extending linearly with respect to the cart.

10. A cart-borne ultrasound system including a movable cart; electronic circuitry. located on the cart which processes ultrasound signals for the formation of ultrasound images, and a display coupled to the circuitry for the display of ultrasound images, comprising:
    a control panel exhibiting a nominal home position and coupled to the electronic circuitry for user control of the ultrasound system;
    a linearly articulating connection coupled to the control panel which permits the control panel to be moved along a lateral path of travel to either side of the home position; and
    a swivel connection coupled to the control panel which permits the control panel to be swiveled about an axis intersecting the control panel at a plurality of locations along the lateral path of travel.

11. The cart-borne ultrasound system of claim 10, wherein the swivel connection permits the control panel to be swiveled about an axis aligned with the forward half of the control panel which is closest to an operator position.

12. The cart-borne ultrasound system of claim 10, wherein the swivel connection operates independently of the linearly articulating connection.

13. The cart-borne ultrasound system of claim 10, further comprising:
    an adjustable translational friction control coupled to the linearly articulating connection; and
    an adjustable rotational friction control coupled to the swivel connection.

14. The cart-borne ultrasound system of claim 13, further comprising a single friction adjustment control, coupled to the adjustable translational friction control and the adjustable rotational friction control, which acts to simultaneously adjust both friction controls.

15. The cart-borne ultrasound system of claim 13, further comprising:
    a swivel bearing and a rotation spring which controls the frictional force required to swivel the control panel; and
    a translation bearing and a translation spring which controls the frictional force required to laterally translate the control panel.

* * * * *